United States Patent
Yoo et al.

(10) Patent No.: US 11,236,117 B2
(45) Date of Patent: Feb. 1, 2022

(54) ALKOXYSILANE COMPOUND OR SALT THEREOF, PREPARATION METHOD THEREFOR, AND HAIR COMPOSITION CONTAINING SAME

(71) Applicant: AMOREPACIFIC CORPORATION, Seoul (KR)

(72) Inventors: Jae Won Yoo, Yongin-si (KR); Yoon Kyun Hwang, Yongin-si (KR); Sung-Ah Bin, Yongin-si (KR); Yong Jin Kim, Yongin-si (KR); John Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/843,511

(22) Filed: Apr. 8, 2020

(65) Prior Publication Data
US 2020/0231609 A1    Jul. 23, 2020

Related U.S. Application Data

(63) Continuation of application No. 15/941,119, filed on Mar. 30, 2018, now abandoned, which is a
(Continued)

(30) Foreign Application Priority Data

Sep. 30, 2015  (KR) .................. 10-2015-0137229
Sep. 23, 2016  (KR) .................. 10-2016-0121880

(51) Int. Cl.
*C07F 7/18*       (2006.01)
*A61K 8/58*       (2006.01)
*A61Q 5/00*       (2006.01)

(52) U.S. Cl.
CPC ............ *C07F 7/1804* (2013.01); *A61K 8/585* (2013.01); *A61Q 5/00* (2013.01)

(58) Field of Classification Search
None
See application file for complete search history.

(56) References Cited

U.S. PATENT DOCUMENTS

4,618,689 A   10/1986  Traver et al.
5,102,930 A    4/1992  Nakazato et al.
(Continued)

FOREIGN PATENT DOCUMENTS

CN   101791278 A    8/2010
EP    0342788 A1   11/1989
(Continued)

OTHER PUBLICATIONS

Ye et al., "Electrochromatographic performance of conventional and polar-embedded C16 silica monolithic stationary phases", J. Sep. Sci., 2010, vol. 33, pp. 3386-3392.
(Continued)

*Primary Examiner* — Clinton A Brooks
(74) *Attorney, Agent, or Firm* — Lucas & Mercanti, LLP

(57) ABSTRACT

The present invention relates to an alkoxysilane salt compound having a novel structure, a preparation method therefor, and a hair composition containing the same. The alkoxysilane salt compound increases the storage stability and the dispersion stability of a hair composition in accordance with the formation of a self-assembly in the aqueous phase and can provide a continuous conditioning effect for hair.

3 Claims, 2 Drawing Sheets

Related U.S. Application Data continuation-in-part of application No. PCT/KR2016/010701, filed on Sep. 23, 2016.

(56) References Cited

U.S. PATENT DOCUMENTS

| | | | |
|---|---|---|---|
| 6,923,953 | B2 | 8/2005 | Malle et al. |
| 7,282,520 | B2 | 10/2007 | Yokomaku et al. |
| 7,909,889 | B2 | 3/2011 | Charrier et al. |
| 7,914,775 | B2 | 3/2011 | Cottard et al. |
| 9,776,020 | B2 | 10/2017 | Bourdin et al. |
| 2003/0177590 | A1 | 9/2003 | Rollant-Corvol et al. |
| 2003/0180440 | A1 | 9/2003 | Elfersy et al. |
| 2009/0326151 | A1 | 12/2009 | Shimizu et al. |
| 2010/0083446 | A1 | 4/2010 | Brun et al. |
| 2014/0205556 | A1 | 7/2014 | Bourdin et al. |

FOREIGN PATENT DOCUMENTS

| | | | |
|---|---|---|---|
| JP | 2001510206 A | | 7/2001 |
| JP | 2003089620 A | | 3/2003 |
| JP | 2003105382 A | | 4/2003 |
| JP | 2004175699 A | | 6/2004 |
| JP | 2004533408 A | | 11/2004 |
| JP | 3611376 B2 | | 1/2005 |
| JP | 2006153507 A | | 6/2006 |
| JP | 2009241290 A | | 10/2009 |
| JP | 2011001344 A | | 1/2011 |
| KR | 10-2009-0030324 A | | 3/2009 |
| KR | 10-2014-0040762 A | | 4/2014 |
| KR | 10-2014-0040764 A | | 4/2014 |
| WO | 03078503 A1 | | 9/2003 |
| WO | WO2011128309 | * | 4/2011 ............... A61Q 5/02 |
| WO | WO2015075236 | * | 11/2014 ............... A61K 8/58 |
| WO | 2015022258 A1 | | 2/2015 |

OTHER PUBLICATIONS

Wang et al., "Synthesis and characterization of novel polar-embedded silica stationary phases for use in reversed-phase high-performance liquid chromatography", Journal of Chromatography A, 2013, vol. 1271, pp. 153-162.

International Search Report for International Application No. PCT/KR2016/010701 (2 Pages) (dated Apr. 12, 2017).

Chemical Abstracts Service; Registry Nos. 1760-24-3 (Nov. 16, 1984), 67674-58-2 (Nov. 16, 1984), 5089-72-5 (Nov. 16, 1984). (Year: 1984).

* cited by examiner (a)

(b)

(c)

(d)

ALKOXYSILANE COMPOUND OR SALT THEREOF, PREPARATION METHOD THEREFOR, AND HAIR COMPOSITION CONTAINING SAME

CROSS-REFERENCE TO RELATED APPLICATIONS

This application is a continuation of U.S. patent application Ser. No. 15/941,119 filed Mar. 30, 2018, which is a continuation-in-part of PCT/KR2016/010701, filed Sep. 23, 2016 which claims the benefit of Korean Patent Application No. 10-2015-0137229, filed Sep. 30, 2015 and Korean Patent Application No., 10-2016-0121880 filed Sep. 23, 2016, the contents of each of which are incorporated herein by reference.

TECHNICAL FIELD

The present invention relates to an alkoxysilane compound or a salt thereof capable of enhancing the stability and conditioning effect of a composition by having a self-aggregating property, a method for preparing the same, and a hair composition containing the same.

BACKGROUND ART

Hair is damaged by the physical stimulation such as repetitive washing and combing and the chemical stimulation such as dyeing and perm. To improve damaged hair, various conditioning compositions such as cationic surfactant, cationic polymer, and silicon compound have been developed, but the durability of the conditioning effect is not sufficient.

Recently, it has been reported that an alkoxysilane compound with an amine group helps to give hair the conditioning effect and the volume feel and there is growing interest in this.

The alkoxysilane compound, which imparts the conditioning effect to hair, not only exhibits limited durability after being applied on the surface of hair but also has problems of stability during storage due to its reactivity with water and non-compatibility with surfactants or components contained in conditioning agents.

To solve these problems, Korean Patent Publication No. 2014-0040762 discloses a composition comprising an alkoxysilane compound, a fatty ester and silicone, and Korean Patent Publication No. 2014-0040764 discloses a composition containing an alkoxysilane and a modified starch.

However, despite these efforts, the alkoxysilane compound still has problems of durability and stability.

PRIOR ART LITERATURE

Korean Patent Application Publication No. 2014-0040762, "COMPOSITION COMPRISING AN ALKOXYSILANE, A FATTY ESTER AND A SILICONE, AND COSMETIC USE THEREOF."

Korean Patent Application Publication No. 2014-0040764, "COMPOSITION COMPRISING AN ALKOXYSILANE AND A MODIFIED STARCH, AND COSMETIC USE THEREOF."

SUMMARY OF THE INVENTION

Accordingly, the inventors of the present invention confirmed that the above problems cannot be solved by adding other components to the alkoxysilane compound according to the prior art, and thus as a result of various studies to solve the above problems, prepared a novel alkoxysilane salt compound having hydrophilicity and hydrophobicity at the same time, and confirmed that this compound improves the stability and conditioning durability of the composition by forming self-aggregates in an aqueous phase, thereby completing the present invention.

Therefore, it is an object of the present invention to provide an alkoxysilane compound or a salt thereof having a novel structure.

In addition, it is another object of the present invention to provide a method for preparing the alkoxysilane compound or the salt thereof.

In addition, it is still another object of the present invention to provide a hair composition comprising the alkoxysilane compound or the salt thereof.

According to an object of the present invention, the present invention provides a compound or a salt thereof comprising an alkoxysilane represented by the following Formula 1:

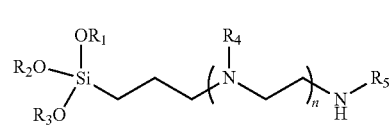

[Formula 1]

wherein $R_1$ to $R_5$ and n are as described in the specification.

In this case, the alkoxysilane salt compound is represented by the following Formula 2 or Formula 3:

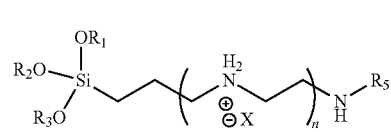

[Formula 2]

wherein $R_1$ to $R_3$, $R_5$, n and X are as described in the specification,

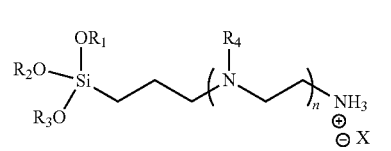

[Formula 3]

wherein $R_1$ to $R_4$, n and X are as described in the specification.

In addition, the present invention provides a method for preparing the alkoxysilane compound of Formula 1 comprising reacting a trialkoxysilyl compound represented by the following Formula 4 with a fatty acid halide represented by the following Formula 5:

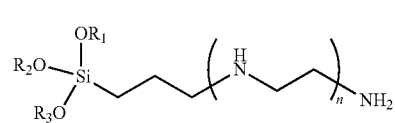

[Formula 4]

wherein $R_1$ to $R_3$, and n are as described in the specification, $$R'—X \qquad \text{[Formula 5]}$$

wherein R' and X are as described in the specification.

In addition, the present invention provides a hair composition comprising the alkoxysilane compound or a salt thereof of Formula 1.

The alkoxysilane compound or the salt thereof of the present invention can form nano-level self-aggregates in the aqueous phase and thus block the direct reaction with water, thereby enhancing the stability in the aqueous phase, which is a problem in the conventional alkoxysilane compounds. Also, due to the hydrophilicity/hydrophobicity characteristics of the alkoxysilane compound, it is possible to improve the dispersion stability of the hair composition, because the miscibility with other components or additives in the hair composition is excellent.

The hair composition according to the present invention can remain after application to hair, thereby providing a continuous conditioning effect and providing a high level of satisfaction in all aspects such as elasticity, softness, shine, and durability.

In addition, this hair composition contains components useful for hair in the self-aggregates, thus enabling the production of products with a variety of functionality.

DETAILED DESCRIPTION OF THE INVENTION

Figure 1:
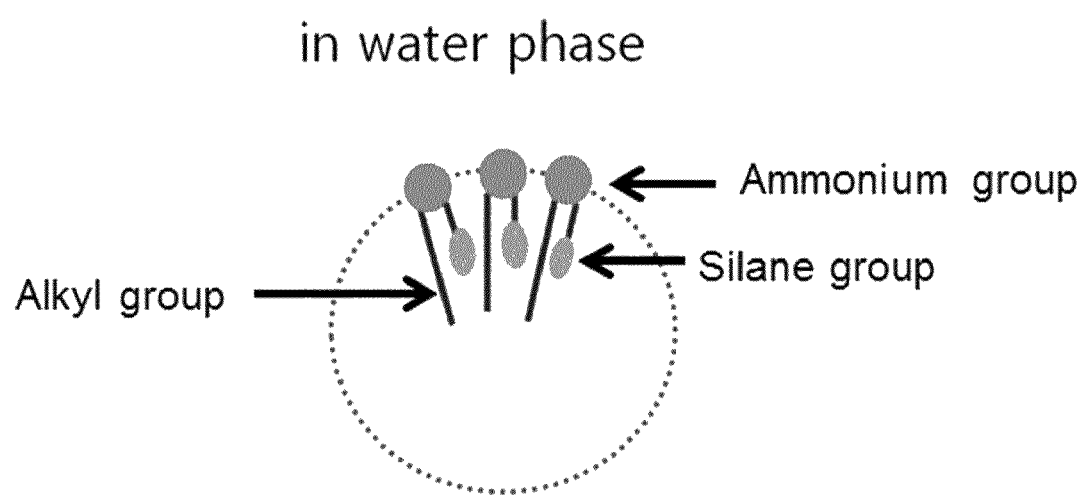
FIG. 1 is a schematic view for explaining formation of self-aggregates of the alkoxysilane salt compound of the present invention.

The present invention suggests a compound of a novel structure capable of producing a composition with an excellent stability due to its self-aggregating property and exhibiting a continuous hair conditioning effect when applied to hair.

Preferably, the present invention provides an alkoxysilane compound or a salt thereof represented by the following Formula 1:

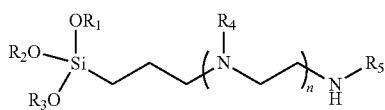

[Formula 1]

wherein $R_1$ to $R_3$ are the same or different from each other and are each independently H, C1-C6 alkyl group or —Si(OR$_6$)$_3$, wherein $R_6$ is H or C1-C6 alkyl group, $R_4$ is H or —C(=O)R$_7$, wherein $R_7$ is C8-C24 alkyl group, $R_5$ is H or —C(=O)R$_8$, wherein $R_8$ is C8-C24 alkyl group and n is an integer of 1 to 10.

As used herein, an alkyl group includes both linear and branched groups unless otherwise specified. For example, the alkyl group may be a methyl group, a ethyl group, a propyl group, a isopropyl group, a butyl group, a pentyl group, a hexyl group, an octyl group, an isooctyl group, a nonyl group, a decyl group, a dodecyl group, an isononanoyl group, a capryl group, a neodecanoyl group, a lauroyl group, a myristoyl group, a palmitoyl group, a stearoyl group, an oleoyl group, a linoleoyl group, a linolenoyl group, an arachidoyl group, a behenoyl group or the like.

Preferably, in Formula 1, $R_1$ to $R_3$ are the same or different from each other and are independently H, a methyl group, a ethyl group or an a propyl group, $R_4$ is H or —C(=O)R$_7$, wherein $R_7$ is C10-C20 alkyl group, and $R_5$ is H or —C(=O)R$_8$, wherein $R_8$ is C10-C20 alkyl group and n is 1 or 2.

In particular, the alkoxysilane salt compound according to the present invention may be prepared in a salt form. Specifically, the —NR$_5$ or —NHR$_4$ in the structure of Formula 1 may be prepared into ammonium salt and the position of the salt may vary depending on the type of the functional group of $R_4$ and $R_5$. In this case, the ammonium salt is advantageously an acid addition salt formed by free acid.

The acid addition salt may be inorganic acids such as hydrochloric acid, nitric acid, phosphoric acid, sulfuric acid, hydrobromic acid, hydroiodic acid, nitrous acid and phosphorous acid; organic acids such as aliphatic mono- and dicarboxylates, phenyl-substituted alkanoates, hydroxy alkanoates and alkanedioates, aromatic acids, aliphatic and aromatic sulfonic acids and the like; and organic acids such as acetic acid, benzoic acid, citric acid, lactic acid, maleic acid, gluconic acid, methane sulfonic acid, 4-toluenesulfonic acid, tartaric acid and fumaric acid.

Preferably, the salt may be an ammonium salt comprising a halogen ion, more preferably an anion comprising F, Cl, Br, or I.

The alkoxysilane compound of the Formula 1 in the present invention contains two amine groups in the molecular structure and has a long alkyl group of a higher fatty acid represented by $R_4$ and $R_5$. Preferably, when $R_4$ is H, $R_5$ is —C(=O)R$_8$ and when $R_5$ is H, $R_4$ is —C(=O)R$_7$.

(i) In the case of $R_4$=H and $R_5$=—C(=O)R$_8$

When $R_4$ is H, the amine at the site connected to it has an ammonium salt form, $R_5$ has a long alkyl group of a higher fatty acid, and the compound may be represented by the following Formula 2:

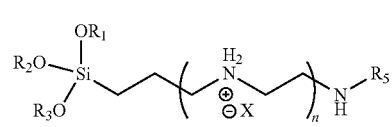

[Formula 2]

wherein $R_1$ to $R_3$, $R_5$, and n are as described above and X is F, Cl, Br, or I.

(ii) In the case of $R_4$=—C(=O)R$_7$ and $R_5$=H

When $R_5$ is H, the amine connected to it has an ammonium salt form, $R_4$ has a long alkyl group of a higher fatty acid, and the compound may be represented by the following Formula 3:

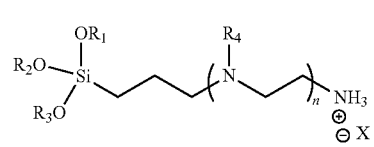

[Formula 3]

wherein $R_1$ to R4, n and X are as described above.

More preferably, the specific embodiment of the alkoxysilane salt compound may be as follows:

(1) [2-(N-hexadecanoylamino)ethyl]-[3-(trimethoxysilyl)propyl]ammonium chloride;
(2) [2-(N-dodecanoylamino)ethyl]-[3-(trimethoxysilyl)propyl]ammonium chloride;
(3) [[2-(N-hexadecanoylamino)ethyl]aminoethyl]-[3-(trimethoxysilyl)propyl]ammonium chloride;
(4) [2-{N-dodecanoyl-[3-(trimethoxysilyl)propyl]amino}]ethylammonium chloride and
(5) 2-{N-hexadecanoyl-[3[-(trimethoxysilyl)propyl]amino]}ethylammonium chloride.

The alkoxysilane salt compound represented by Formula 1 may be provided in the form of a hydrate or solvate.

The alkoxysilane salt compound of Formula 1 has both the higher fatty acid alkyl group of the long alkyl group having the hydrophobicity and the ammonium salt having the hydrophilicity in the molecular structure, so that the compound has an activity at the interface between solid/gas, solid/liquid, solid/solid, liquid/gas and liquid/liquid. As shown in FIG. 1, the alkoxysilane salt compound of formula 1 forms self-aggregates in the environment of the water phase. At this time, the siloxane group and the alkyl group with hydrophobicity are arranged inside the self-aggregate and the ammonium group with the hydrophilicity is arranged outside the self-aggregate. This self-aggregating property is advantageous as long as the alkyl group of the higher fatty acid is longer.

In addition, the alkoxysilane compound or the salt thereof of Formula 1 according to the present invention may be prepared by reacting a trialkoxysilyl compound represented by the following Formula 4 with a fatty acid halide represented by the following Formula 5:

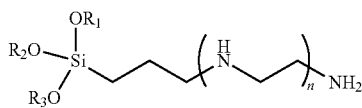
[Formula 4]

wherein $R_1$ to $R_3$, and n is as described above.

R'—X [Formula 5]

wherein R' is H or —C(=O)R", wherein R" is C8-C24 alkyl group and X is as described above.

The trialkoxysilyl compound of Formula 4 is a compound having an amine group in the molecular structure and may be any of those satisfying the definitions of $R_1$ to $R_3$ and n, which may be prepared directly or may be a commercially available substance. For example, the trialkoxysilyl compound may be N-[3-(trimethoxysilyl)propyl]-ethylenediamine, N-[3-(triethoxysilyl)propyl]-ethylenediamine, N-[3-(trimethoxysilyl)propyl]-diethylenetriamine or N-[3-(triethoxysilyl)propyl]-diethylenetriamine.

The fatty acid halide of Formula 5 can be any that can produce ammonium salt by binding to the amine of the trialkoxysilyl compound of Formula 4. For example, the fatty acid halide may comprise at least one selected from the group consisting of isononanoyl chloride, capryl chloride, neodecanoyl chloride, lauroyl chloride, myristoyl chloride, palmitoyl chloride, stearoyl chloride, oleoyl chloride, linoleoyl chloride, linolenoyl chloride, arachidoyl chloride, and behenoyl chloride. Preferably the fatty acid halide may be palmitoyl chloride or lauroyl chloride.

In this case, the salt may be obtained in the form of an ammonium salt and the alkoxysilane compound of Formula 1 can be prepared by removing the halogen X. In this case, the removal of X is not particularly limited in the present invention and can be prepared by a known method.

In particular, the compound of Formula 1 may be prepared in the form of a salt compound of Formula 2 or Formula 3, which can be performed in largely two ways according to the definitions of $R_4$ and $R_5$.

(i) In the case of $R_4$=H and $R_5$=—C(=O)$R_8$ [salt of Formula 2]

The preparation of the alkoxysilane salt compound of Formula 2 may be performed by the reaction of a compound of Formula 4 with a fatty acid halide of Formula 6, as shown in the following Scheme 1:

[Scheme 1]

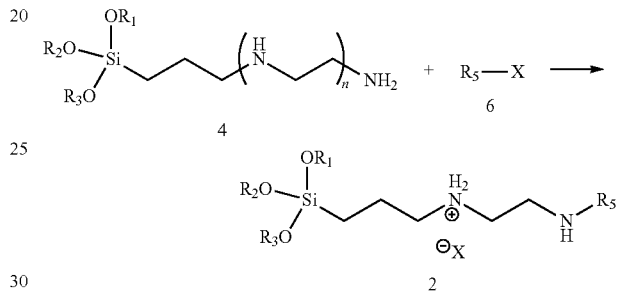

wherein $R_1$ to $R_3$, $R_5$, n and X are as described above.

The compound of Formula 4 is as described above.

The fatty acid halide $R_5$—X of Formula 6 is for satisfying the definition of $R_5$ and X and is as described above for R'—X.

This reaction may be carried out in a solvent, and the solvent is not particularly limited in the present invention and may be an aliphatic hydrocarbon solvent such as hexane, heptane or cyclohexane; a halogenated hydrocarbon solvent such as chloroform, tetrachloroethylene, carbon tetrachloride, dichloromethane or dichloroethane; propylene carbonate, ethylene carbonate, dimethylcarbonate, dibutylcarbonate, ethylmethylcarbonate, nitromethane, nitrobenzene, etc.; a ketone solvent such as acetone, methylethylketone, methylisobutylketone or cyclohexanone; an amide solvent such as N-methyl-2-pyrrolidinone, 2-pyrrolidinone, N-methylformamide or N,N-dimethylformamide; a sulfoxide solvent such as dimethylsulfoxide or diethylsulfoxide; a sulfone solvent such as diethylsulfone or tetramethylene sulfone; a nitrile solvent such as acetonitrile or benzonitrile; an amine solvent such as alkylamine, cyclic amine or aromatic amine; an ester solvent such as methyl butylate, ethyl butylate or propylpropionate; a carboxylic ester solvent such as ethyl acetate or butyl acetate; or an aromatic hydrocarbon solvent such as benzene, ethylbenzene, chlorobenzene, toluene or xylene, and for example, may be dichloromethane.

The organic solvent may be used alone or in a mixture of two or more and may be used in an amount of from 10 to 100 parts by weight, based on 1 part by weight of the compound of Formula 6 so that the reaction can be sufficiently carried out.

The reaction may be carried out at a low temperature of from −4 to 40° C., more preferably from 0 to 10° C., and preferably may be carried out for 30 minutes to 3 hours, more preferably for 1 to 2 hours. When crystals are precipitated after the reaction, the salt of Formula 2 can be obtained through filtration.

(ii) In the case of $R_4 = -C(=O)R_7$ and $R_5 = H$ [salt of Formula 3]

The alkoxysilane salt compound represented by Formula 3 may be prepared comprising the steps of, as shown in the following Scheme 2:

introducing a protecting group (PG) into the primary amine of the trialkoxysilyl compound represented by Formula 4 in the presence of a base;

reacting the compound of Formula 7 with the introduced protecting group with the fatty acid halide of Formula 8 and removing the protecting group from the obtained compound of Formula 9.

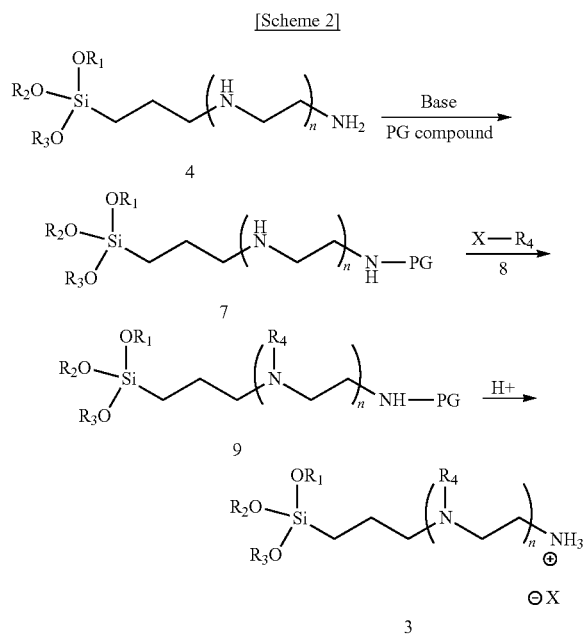

[Scheme 2]

wherein $R_1$ to $R_4$, n and X are as described above.

The protecting group (PG) is used to protect the terminal amine group, in order to form the ammonium salt in the molecular structure rather than at the terminal as in Scheme 1 above. The protecting group PG which can be used may be Bz (benzyl), Trt (trityl), Boc (t-butyloxycarbonyl), Ac (acetate), Cbz (carboxybenzyl), or Fmoc (9-fluorenyl methoxycarbonyl), and preferably may be Boc.

In the reaction, the base may comprise at least one selected from the group consisting of trimethylamine, triethylamine, tripropylamine, tributylamine, tripentylamine, trioctylamine, tribenzylamine, sodium hydroxide, potassium hydroxide, lithium hydroxide, calcium hydroxide, sodium carbonate, potassium carbonate, sodium hydrogen carbonate and potassium hydrogen carbonate, and preferably may be triethylamine.

The fatty acid halide of Formula 8 may be selected from the fatty acid halides as mentioned in Scheme 1, and preferably may be palmitoyl chloride or lauroyl chloride.

In this case, the reaction temperature, reaction time, solvent and the like are as described in Scheme 1 above.

The protecting group at the terminal is removed from the compound of Formula 9 obtained after the reaction. In this case, the removal of the protecting group is not particularly limited in the present invention, can be removed by a known method, and may be carried out in different ways depending on the kind of the protecting group.

For example, Boc can be removed by treatment with an acid such as hydrochloric acid, sulfuric acid, methane sulfonic acid, phosphoric acid, bromic acid, nitric acid, nitrous acid, trifluoroacetic acid, acetic acid and the like. In addition, Boc can be eliminated by catalytic hydrogenation treatment via hydrogen injection under the pressure of 1-2 atm in the presence of a Pd/C catalyst.

Usage

As mentioned above, the alkoxysilane salt compounds form self-aggregates, as shown in FIG. 1, and thus can be used in a variety of applications requiring them.

Preferably, the alkoxysilane salt compound of Formula 1 can be used in a hair composition.

Most conventional alkoxysilane compounds exist in liquid form and have limited durability after application on the surface of hair and have a problem of low stability and poor compatibility with other components (e.g. surfactant, and conditioning agent component) during storage. Therefore, the alkoxysilane compounds or the salts thereof, into which a higher fatty acid is introduced according to the present invention, can form the self-aggregates in the water phase, and thus can have the high stability in the composition and can have the hydrophilicity and hydrophobicity functional groups in the molecular structure, thereby having the excellent miscibility (or compatibility) with other components, and thus enhancing the stability of the composition and further enhancing the durability of active components such as the conditioning agents.

The alkoxysilane compound or the salt thereof of the Formula 1 of the present invention may be included in an amount of from 0.001 to 15% by weight, preferably from 0.1 to 10% by weight, based on the total hair composition. When the content is less than the above range, the above-mentioned effect cannot be ensured. On the other hand, when the content is in excess of the above range, the stability of the composition may be lowered or the soft and sticky feeling of use is exhibited. Therefore, the alkoxysilane compound or the salt thereof is suitably used within the above range.

In particular, the self-aggregates having a diameter of from 50 to 500 nm, preferably from 100 to 400 nm may be formed by the alkoxysilane compound or the salt thereof of Formula 1, and it can be expected that components useful for hair, such as components which can alleviate hair loss or components which can aid in hair health, may be carried within the self-aggregates and thus be delivered.

The component useful for hair which can be carried may be at least one selected from the group consisting of minoxidil, 4-pyrrolidine 2,6-diaminopyrimidine-1-oxide, biota seed, vitamin B5 derivatives (panthenol derivatives), Swertia herb extract (Swertiall), coix, licorice extract (glycyrrhizin and glycyrrhetic acid), niacinamide, vitamin E derivatives, adenosine, glyceryl pentadecanoate, benzylaminopurine (6-benzylaminopurine), Eugenol, Saw palmetto, dialkylmonoamine derivatives, isoflavones, Hinokitiol and benzyl nicotinate, but is not limited thereto.

The hair composition comprising the alkoxysilane salt compound and the useful components can be applied as any formulation that can be used for hair, such as hair shampoo, hair rinse, hair conditioner, hair cream, hair lotion, scalp pack, hair tonic, hair nutrition lotion, hair treatment, hair ampoule, hair serum, hair mousse, hair wax, hair spray, styling gel or scalp treatment.

In the respective formulations, components other than the essential components described above can be appropriately selected and mixed according to the type of the external preparation or the purpose of use by those skilled in the art without difficulty.

For example, silicon compounds such as cyclomethicone, dimethicone, phenyltrimethicone, amodimethicone, polydimethylsiloxane, phenyl siloxane, alkylmethylsiloxane, and dimethicone copolyol can be used.

In addition to the silicon compounds, preservatives, thickeners, viscosity regulators, pH adjusting agents, perfumes, etc., which are widely known and used by a person skilled in the art can be further contained as a typical optional component for maintaining basic physical properties and quality, and deionized water, an organic solvent or the like may be contained as a solvent.

For example, the organic solvent may include n-butylalcohol, t-butylalcohol, benzylalcohol, phenethylalcohol, hexylalcohol, isopropylalcohol, methylalcohol, oleylalcohol, propylalcohol, cyclohexanedimethanol, phenoxyethanol, butoxyethanol, dethoxyethanol, methoxyethanol, methoxyelglycol, butyleneglycol, propyleneglycol, pentyleneglycol, hexyleneglycol, benzylglycol, diethyleneglycol, dipropyleneglycol, 1,2-butanediol, 1,4-butanediol, 2,3-butanediol, propanediol, 1,5-pentanediol, isopentyldiol, ethylhexanediol, 1,2-hexanediol, 1,2,6-hexanetriol, 1,10-decanediol, 3-methoxybutanol, methoxyisopropanol, methoxymethylbutanol, ethylene carbonate, propylene carbonate and a mixture thereof.

The preservative may include mixture of methyl paraoxybenzoates, methylparaben, butylparaben, ethylparaben, propylparaben, benzylalcohol, phenoxyethanol, phenoxyisopropanol, phenylpropanol, methylchloroisothiazolinone and methylisothiazolinone.

The thickener or viscosity regulator may include fatty acid alcohol, fatty acid, hydroxypropylmethylcellulose, hydroxymethylcellulose, sodium chloride, ammonium chloride, propyleneglycol, and hexyleneglycol.

The pH adjusting agent may include acetic acid, adipic acid, aminoethyl propanediol, aminomethyl propanediol, aminomethyl propanol, am inopropanediol, ascorbic acid, azelaic acid, benzoic acid, butyl diethanol amine, butylethanolamine, citric acid, dibutyl ethanolamine, diethanolamine, diisopropylamine, diisopropanolamine, dimethyl isopropanolamine, methyl ethanolamine, fumaric acid, galacturonic acid, glutaric acid, glycolic acid, isopropanolamine, isopropylamine, maleic acid, malic acid, malonic acid and methylethanolamine.

In this case, the selection of each component and its content are not particularly limited in the present invention but can be appropriately selected by a person having ordinary skill in the art, and for example, may be included within the range of from 0.001 to 10% by weight.

EXAMPLES

Hereinafter, examples for facilitating understanding of the present invention will be described. The following examples are merely examples related to the effects of the present invention, and the scope and effect of the present invention are not limited thereto.

Preparation Example 1: Preparation of [2-(N-hexadecanoylamino)ethyl]-[3-(trimethoxysilyl)propyl] ammonium chloride

[Formula 12]

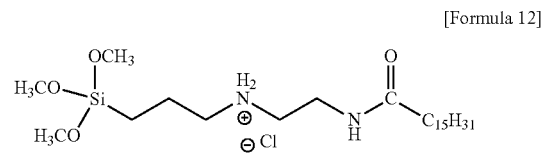

6.67 g (30 mmol) of N-[3-(trimethoxysilyl)propyl]-ethylenediamine was dissolved in dichloromethane and then 9.15 mL (30 mmol) of palmitoyl chloride was slowly added dropwise while stirring in an ice bath. After 30 minutes, the reaction product obtained after completion of the reaction was distilled under reduced pressure, followed by addition of diethyl ether to perform a precipitation reaction. The precipitated solid was filtered and dried to obtain 13.8 g (yield: 92%) of the compound of Formula 12 as a white solid.

$^1$H-NMR (ppm): δ 0.73, 0.88, 1.24, 1.57, 2.23, 3.21, 3.55, 3.64

Preparation Example 2: Preparation of [2-(N-dodecanoylamino)ethyl]]-[3-(trimethoxysilyl)propyl] ammonium chloride

[Formula 13]

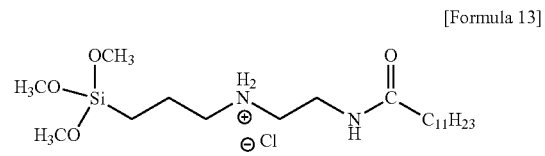

6.67 g (30 mmol) of N-[3-(trimethoxysilyl)propyl]-ethylenediamine was dissolved in dichloromethane and then 6.9 mL (30 mmol) of lauroyl chloride was slowly added dropwise while stirring in an ice bath. After 30 minutes, the reaction product obtained after completion of the reaction was distilled under reduced pressure, followed by addition of diethyl ether to perform a precipitation reaction. The precipitated solid was filtered and dried to obtain 12.0 g (yield: 90%) of the compound of Formula 13 as a white solid.

$^1$H-NMR (ppm): δ 0.73, 0.88, 1.25, 1.56, 2.25, 3.21, 3.55, 3.68

Preparation Example 3: Preparation of [[2-(N-hexadecanoylamino)ethyl]aminoethyl]-[3-(trimethoxysilyl)propyl]ammonium chloride

[Formula 14]

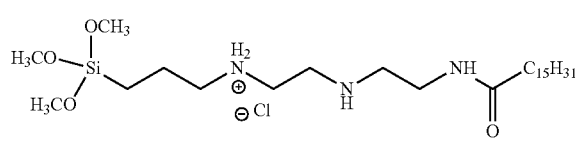

7.96 g (30 mmol) of N-[3-(trimethoxysilyl)propyl]-diethylenetriamine was dissolved in dichloromethane and then 9.15 mL (30 mmol) of palmitoyl chloride was slowly added dropwise while stirring in an ice bath. After 30 minutes, the reaction product obtained after completion of the reaction was distilled under reduced pressure, followed by addition of diethyl ether to perform a precipitation reaction. The precipitated solid was filtered and dried to obtain 14.2 g (yield: 90%) of the compound of Formula 14 as a white solid.

$^1$H-NMR (ppm): δ 0.73, 0.89, 1.25, 1.56, 2.24, 2.74, 3.23, 3.57, 3.65

Preparation Example 4: Preparation of [2-{N-dodecanoyl-[3-(trimethoxysilyl)propyl]amino}]ethylammonium chloride

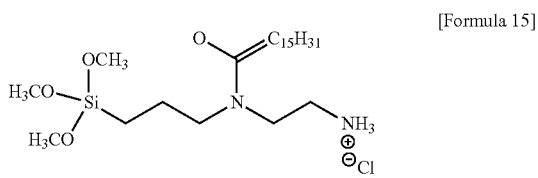

[Formula 15]

6.67 g (30 mmol) of N-[3-(trimethoxysilyl)propyl]-ethylenediamine and 4.6 mL (33 mmol) of triethylamine were dissolved in dichloromethane and then a solution in which 7.2 g (30 mmol) of di-tert-butyl dicarbonate was dissolved was slowly added dropwise while stirring in an ice bath. To the reaction mixture, 9.15 mL (30 mmol) of palmitoyl chloride was slowly added dropwise to carry out the reaction.

Then, the obtained reaction product was distilled under reduced pressure, diethyl ether was added, and filtration was carried out. The filtrate was collected, concentrated, and then stirred in HCl methanol solution. After 30 minutes, the reaction product obtained after completion of the reaction was distilled under reduced pressure, followed by addition of diethyl ether to perform a precipitation reaction. The precipitated solid was filtered and dried to obtain 10.9 g (yield: 73%) of the compound of Formula 15 as a white solid.

$^1$H-NMR (ppm): δ 0.72, 0.87, 1.24, 1.59, 2.26, 3.20, 3.52, 3.61

Preparation example 5: Preparation of 2-{N-hexadecanoyl-[3[-(trimethoxysilyl)propyl]amino]}ethyl-ammonium chloride

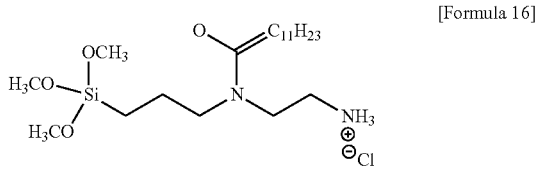

[Formula 16]

6.67 g (30 mmol) of N-[3-(trimethoxysilyl)propyl]-ethylenediamine and 4.6 mL (33 mmol) of triethylamine were dissolved in dichloromethane and then a solution in which 7.2 g (30 mmol) of di-tert-butyl dicarbonate was dissolved was slowly added dropwise while stirring in an ice bath. To the reaction mixture, 6.9 mL (30 mmol) of lauroyl chloride was slowly added dropwise to carry out the reaction.

Then, the obtained reaction product was distilled under reduced pressure, diethyl ether was added, and filtration was carried out. The filtrate was collected, concentrated, and then stirred in HCl methanol solution. After 30 minutes, the reaction product obtained after completion of the reaction was distilled under reduced pressure, followed by addition of diethyl ether to perform a precipitation reaction. The precipitated solid was filtered and dried to obtain 9.6 g (yield: 72%) of the compound of Formula 16 as a white solid.

$^1$H-NMR (ppm): δ 0.73, 0.88, 1.25, 1.56, 2.25, 3.21, 3.55, 3.68

Experimental Example 1: Confirmation of Self-Aggregate Formation and Stability

The salts of Preparation example 1 to Preparation example 5 were added to dichloromethane and dissolved by heating, respectively, and the resulting solutions were slowly added dropwise to deionized water at 60 to 70° C. while stirring. After completion of the stirring, the solvents in the reaction solutions obtained were removed by distillation under reduced pressure to prepare self-aggregated sample. The particle size of the self-aggregates was observed using a Zetasizer at the time of preparation and three days after preparation of the obtained samples. The results are shown in Table 1 below.

TABLE 1

| Item | At the time of preparation | Three days after preparation |
| --- | --- | --- |
| Preparation example 1 | 263 nm | 266 nm |
| Preparation example 2 | 247 nm | 259 nm |
| Preparation example 3 | 281 nm | 288 nm |
| Preparation example 4 | 267 nm | 265 nm |
| Preparation example 5 | 253 nm | 263 nm |

Referring to Table 1, all the compounds of preparation examples 1 to 5 formed self-aggregates with a diameter of 200 to 300 nm.

Additionally, when comparing the sizes of the self-aggregates at the time of preparation and 3 days after preparation, it is identified that the particle size after 3 days has not changed greatly and thus the stability is excellent.

Due to the formation of this self-aggregate, the alkoxysilane group is placed in the hydrophobicity part in the self-aggregate, thereby reducing the contact with water, and thus improving the stability during storage. In addition, it is judged that the longer the alkyl group, the more effective this tendency is.

Example 1, Example 2, and Comparative Example 1: Preparation of Treatment Formulation The hair compositions of the treatment formulations including the compounds of Preparation example 1 and Preparation example 2 described above in the composition of the following Table 2 respectively were prepared according to a known method.

TABLE 2

| Component (% by weight) | Example 1 | Example 2 | Comparative Example 1 |
|---|---|---|---|
| Compound of Preparation example 1 | 0.5 | 0 | 0 |
| Compound of Preparation example 2 | 0 | 0.5 | |
| Steartrimonium chloride | 0.5 | 0.5 | 1.0 |
| Glycerin | 5.0 | 5.0 | 5.0 |
| Lactic acid | 0.3 | 0.3 | 0.3 |
| Cetearyl alcohol | 3.0 | 3.0 | 3.0 |
| Dimethicone & silane | 3.0 | 3.0 | 3.0 |
| Phenoxyethanol | 0.3 | 0.3 | 0.3 |
| Perfume | 0.3 | 0.3 | 0.3 |
| Purified water | To 100 | To 100 | To 100 |

Experimental Example 2: Evaluation of Hair Residual Force

The wool clothes were treated with 1 g of the hair compositions prepared in the above Examples and Comparative examples respectively, followed by thoroughly washing with water at 30 to 35° C., and then repeatedly washed three times with a certain amount of shampoo.

Figure 2:
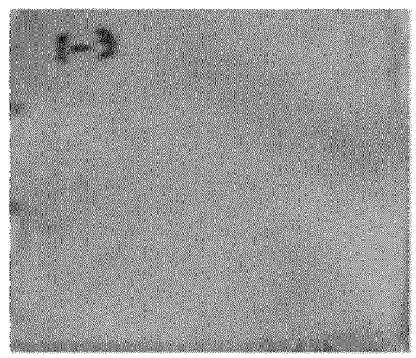
FIG. 2 is an image showing the results of colorimetric measurement of Experimental example 2, which means (a) no treatment group, (b) the compositions of Comparative example 1, (c) the compositions of Example 1 and (d) the compositions of Example 2.
Figure 2:
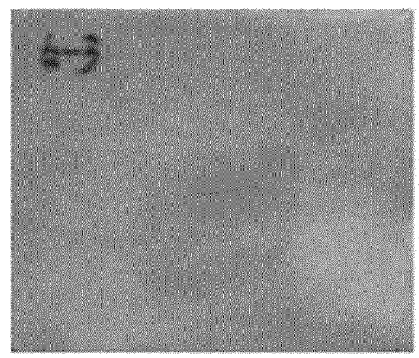
Figure 2:
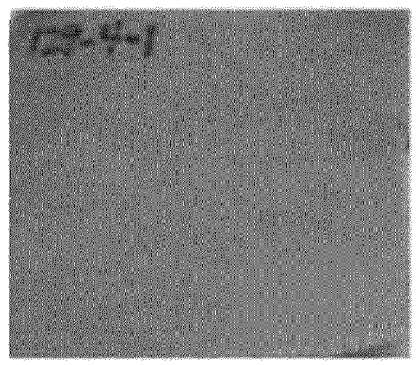
Figure 2:
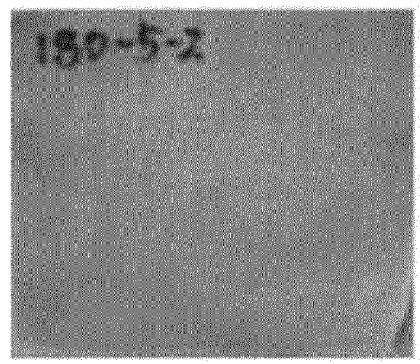

Wool clothes washed with water and wool clothes washed three times with shampoo were immersed and stained in a 0.5% Rubin dye solution for 3 minutes and then were evaluated for residual force in hair using red color (a value) by colorimeter. The results are shown in Table 3 and FIG. 2. In this case, the untreated group refers to the wool cloth as a control group with no treatment. Since the Rubin dye is an anionic dye and is ionically bound to a cationic polymer or a composite of cationic polymer-anionic surfactant adsorbed on the hair, the residual amount of Rubin dye on the hair can be estimated by measuring the degree of staining. At this time, it means that the higher the value of a, the higher the amount of residual adsorbed on the hair.

TABLE 3

| Item | Value (a) by colorimeter after washing with shampoo three times |
|---|---|
| Untreated group | 4.0 |
| Composition of Comparative example 1 | 11.1 |
| Composition of Example 1 | 17.6 |
| Composition of Example 2 | 16.3 |

Referring to Table 3, the compositions of Examples 1 and 2 comprising the alkoxysilane salt compounds according to the present invention showed an improvement on the effect of about 4 to 5 times the level of the untreated group.

In addition, it is identified that the residual force in the hair after shampoo cleaning can be improved compared to the composition of Comparative example 1 which did not contain an alkoxysilane salt compound, thereby exhibiting the continuous conditioning effect.

Experimental Example 3: Evaluation of Satisfaction

The overall satisfaction for the hair elasticity, softness, shine, and style persistence by the hair compositions prepared in the above Examples and Comparative examples was evaluated by a panel of 20 experts.

Satisfaction level for each item was evaluated by the scale of 1, 3, 5, 7, and 9 points (the higher the score, the higher the satisfaction), and then each point was totaled to obtain an average (satisfaction), and the results are shown in Table 4 below.

TABLE 4

| Item | Comparative example 1 | Example 1 | Example 2 |
|---|---|---|---|
| Elasticity | 2.8 | 4.3 | 4.5 |
| Softness | 2.9 | 5.8 | 5.5 |
| Shine | 2.9 | 4.2 | 4.1 |
| Persistence | 2.6 | 6.8 | 6.1 |
| Satisfaction | 2.7 | 6.1 | 5.7 |

Referring to Table 4, it was identified that the hair compositions of Examples 1 and 2 including the alkoxysilane salt compound according to the present invention exhibited excellent results in all of the elasticity, softness, shine, and persistence as compared to Comparative example 1, and the satisfaction was improved.

Hereinafter, although further formulation examples of the present invention are described, the formulations of hair composition comprising the alkoxysilane salt compound according to the present invention are not limited to these examples.

Formulation Example 1: Scalp Hair Tonic

A scalp hair tonic was prepared in a conventional manner according to the composition as described below.

TABLE 5

| | Content (% by weight) |
|---|---|
| Compound of Preparation example 1 | 0.5 |
| Menthol | 0.1 |
| D-Panthenol | 0.6 |
| Salicylic acid | 0.05 |
| Glycerin | 1.0 |
| Polyoxyethylene hardened castor oil | 0.8 |
| Tocopherol acetate | 0.03 |
| Combined perfume | q.s. |
| Ethanol | 30.0 |
| Purified water | remainder |

Formulation Example 2: Scalp Essence

A scalp essence was prepared in a conventional manner according to the composition described below.

TABLE 6

| | Content (% by weight) |
|---|---|
| Compound of Preparation example 1 | 0.5 |
| Ethanol | 30.0 |
| Polysorbate 60 | 1.5 |
| Glycerin | 3.0 |
| Carboxyvinyl polymer | 0.1 |
| Triethanolamine | 0.2 |
| Preservative | q.s. |
| Perfume and pigment | q.s. |
| Purified water | remainder |

The invention claimed is:

1. A method for providing a continuous hair conditioning effect comprising:
  applying a hair composition to a subject in need thereof
    wherein the hair composition comprises an alkoxysilane salt compound selected from the group consisting of:

(1) [2-(N-hexadecanoylamino)ethyl]-[3-(trimethyoxysilyl)propyl]ammonium chloride;
(2) [2-(N-dodecanoylamino)ethyl]-[3-(trimethoxysilyl)propyl]ammonium chloride;
(3) [[2-(N-hexadecanoylamino)ethyl]-[3-(trimethoxysilyl)propyl]ammonium chloride;
(4) [2-{N-dodecanoyl-[3-(trimethoxysilyl)propyl]amino}]ethylammonium chloride and
(5) 2-{N-hexadecanoyl- [3[-(trimethoxysilyl)propyl]amino]}ethylammonium chloride

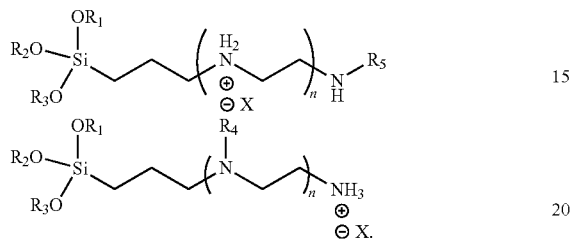

2. The method according to claim 1, wherein the alkoxysilane salt compound has self-aggregating property.

3. The method according to claim 1, wherein the alkoxysilane salt compound is included in an amount of from 0.001 to 15% by weight, based on the total weight of the hair composition.

* * * * *